United States Patent
Akagane (10) Patent No.: US 9,439,671 B2
(45) Date of Patent: Sep. 13, 2016

(54) ULTRASONIC TREATMENT SYSTEM

(71) Applicant: OLYMPUS CORPORATION, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/674,009

(22) Filed: Mar. 31, 2015

(65) Prior Publication Data

US 2015/0201960 A1   Jul. 23, 2015

Related U.S. Application Data

(63) Continuation of application No. PCT/JP2014/062141, filed on May 2, 2014.

(60) Provisional application No. 61/818,657, filed on May 2, 2013.

(51) Int. Cl.
| | |
|---|---|
| B06B 1/06 | (2006.01) |
| A61B 17/32 | (2006.01) |
| A61B 18/00 | (2006.01) |
| A61B 17/00 | (2006.01) |

(52) U.S. Cl.
CPC ......... A61B 17/320092 (2013.01); B06B 1/06 (2013.01); *A61B 2017/0019* (2013.01); *A61B 2017/00132* (2013.01); *A61B 2017/00199* (2013.01); *A61B 2017/00411* (2013.01); *A61B 2018/00607* (2013.01); *A61B 2560/0475* (2013.01)

(58) Field of Classification Search
CPC ............ A61B 17/320092; B06B 1/06; B06B 1/0603
USPC ......................................... 310/322, 334, 335
See application file for complete search history.

(56) References Cited

U.S. PATENT DOCUMENTS

| | | | |
|---|---|---|---|
| 2011/0034910 A1 | 2/2011 | Ross et al. | |
| 2011/0062824 A1* | 3/2011 | Wada | B06B 1/0622 |
| | | | 310/334 |
| 2011/0082486 A1* | 4/2011 | Messerly | A61B 17/320092 |
| | | | 606/169 |

FOREIGN PATENT DOCUMENTS

| | | |
|---|---|---|
| JP | S57-49426 A | 3/1982 |
| JP | H05-049647 A | 3/1993 |
| JP | H11-56746 A | 3/1999 |
| JP | 2003-038423 A | 2/2003 |
| JP | 2007-244403 A | 9/2007 |
| JP | 2011-036655 A | 2/2011 |

OTHER PUBLICATIONS

Jun. 17, 2014 International Search Report issued in International Application No. PCT/JP2014/062141.
Nov. 12, 2015 mailed English translation of International Preliminary Report on Patentability issued in International Patent Application No. PCT/JP2014/062141.

\* cited by examiner

*Primary Examiner* — Derek Rosenau
(74) *Attorney, Agent, or Firm* — Oliff PLC (57) ABSTRACT

An ultrasonic treatment system includes a calculator calculating a relation between an amplitude of a vibrating body unit when an ultrasonic vibration is generated and an electric current to be supplied to an ultrasonic generator based on both an elapse of time and a number of thermal processes. The ultrasonic treatment system includes a current value setting section setting the electric current to an adaptive current value that brings the amplitude of the vibrating body unit to a target amplitude based on the relation between the amplitude of the vibrating body unit and the electric current calculated by the calculation section.

9 Claims, 6 Drawing Sheets

ULTRASONIC TREATMENT SYSTEM

CROSS-REFERENCE TO RELATED APPLICATIONS

This is a Continuation Application of PCT Application No. PCT/JP2014/062141, filed May 2, 2014 and based upon and claiming the benefit of priority from prior U.S. Provisional Application No. 61/818,657, filed May 2, 2013, the entire contents of which are incorporated herein by reference.

BACKGROUND OF THE INVENTION

1. Field of the Invention

The present invention relates to an ultrasonic treatment system including an ultrasonic treatment instrument configured to perform a treatment by an ultrasonic vibration.

2. Description of the Related Art

Jpn. Pat. Appln. KOKAI Publication No. 5-49647 has disclosed an ultrasonic treatment system provided with a vibrating body unit including an ultrasonic vibrator which is an ultrasonic generator, and a probe which is configured to transmit an ultrasonic vibration from a proximal direction to a distal direction. In this ultrasonic treatment system, a vibration sensor is attached to the vibrating body, and the vibrating state of the vibrating body unit is detected by the vibration sensor. A recording section is then configured to calculate a vibrating time of the vibrating body unit (i.e., an used time of an ultrasonic treatment instrument) and the amplitude of the ultrasonic vibration relative to the current value of an electric current to be supplied from the vibrating state of the vibrating body unit, and configured to record information regarding the used time of the ultrasonic treatment device and the amplitude of the ultrasonic vibration relative to the current value of the electric current. The used state of the vibrating body unit is recognized on the basis of the recorded information, and whether a handpiece which is the ultrasonic treatment instrument including the vibrating body unit has exceeded its life is judged. If the handpiece has exceeded its life, a warning is issued, or the supply of the electric current to the ultrasonic vibrator is stopped.

BRIEF SUMMARY OF THE INVENTION

According to one aspect of the invention, an ultrasonic treatment system includes that: a vibrating body unit including an ultrasonic generator configured to generate an ultrasonic vibration when supplied with an electric current, and an ultrasonic transmitting portion configured to transmit the generated ultrasonic vibration; a storage section configured to store an elapse of time since a production of the vibrating body unit and a number of thermal processes conducted every sterilization of the vibrating body unit; a calculation section configured to calculate the relation between the amplitude of the vibrating body unit when the ultrasonic vibration is generated and the electric current to be supplied to the ultrasonic generator on the basis of both the elapse of time and the number of thermal processes; a current value setting section configured to set the electric current to be supplied to the ultrasonic generator to an adaptive current value that brings the amplitude of the vibrating body unit to a target amplitude to perform an optimum vibration on the basis of the relation between the amplitude of the vibrating body unit and the electric current calculated by the calculation section; and a supply control section configured to control a supply of the electric current to the ultrasonic generator so that the electric current having the adaptive current value is supplied.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

A first embodiment of the present invention is described with reference to FIG. 1 to FIG. 5.

Figure 1:
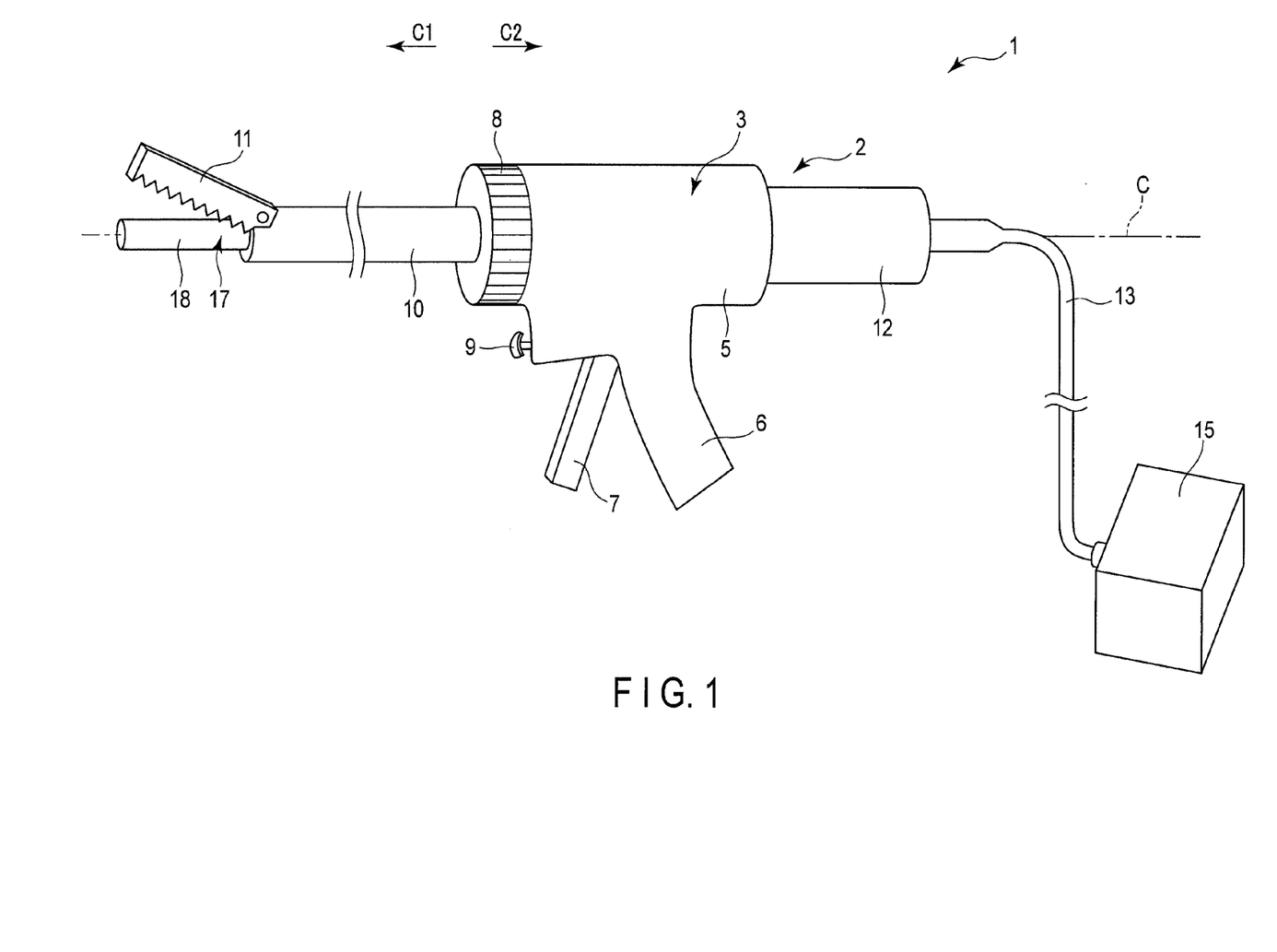
FIG. 1 is a perspective view schematically showing an ultrasonic treatment system according to a first embodiment.
Figure 2:
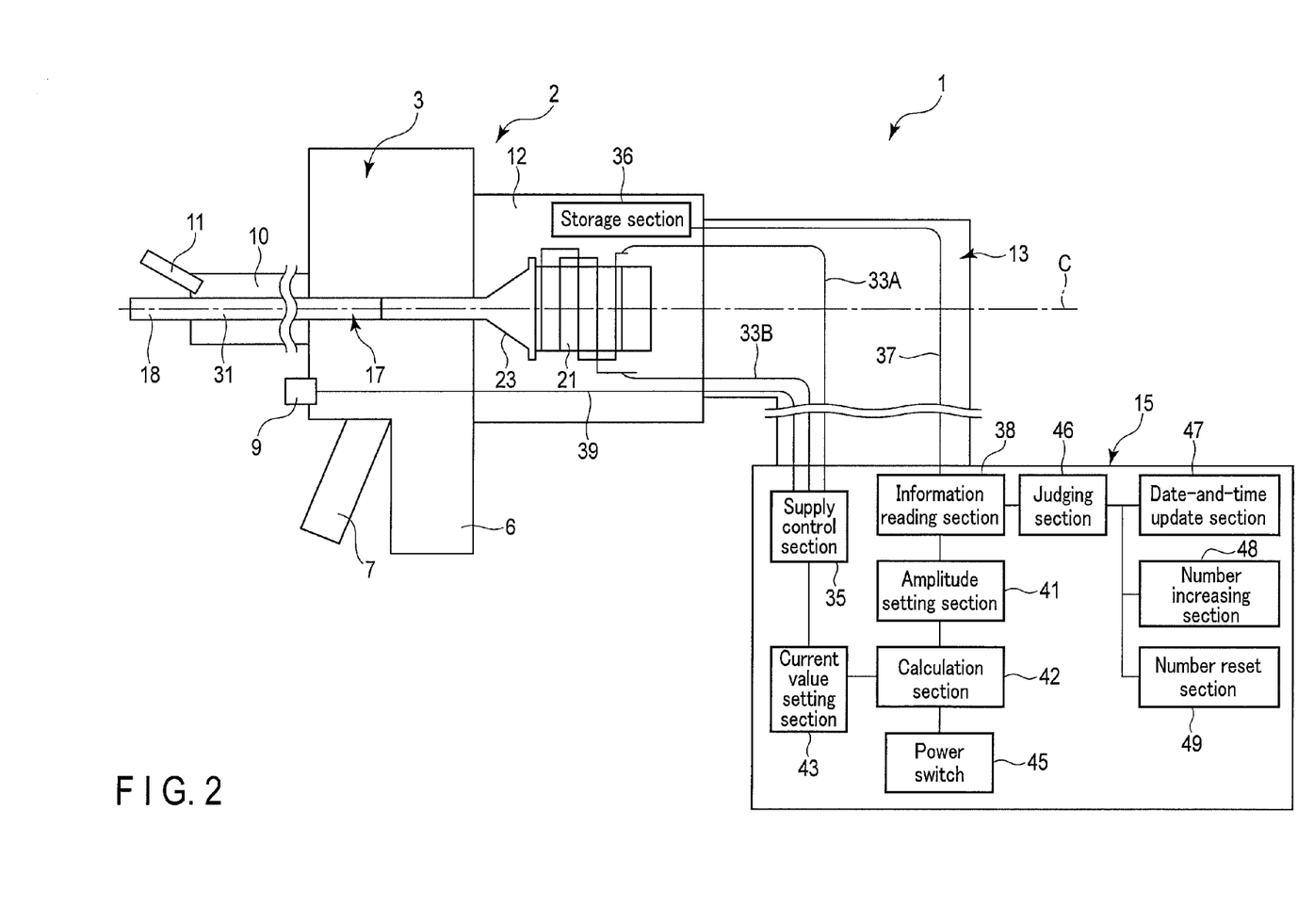
FIG. 2 is a block diagram schematically showing the ultrasonic treatment system according to the first embodiment.

FIG. 1 and FIG. 2 are diagrams showing the configuration of an ultrasonic treatment system 1 according to the present embodiment. As shown in FIG. 1, the ultrasonic treatment system 1 includes a handpiece 2 which is an ultrasonic treatment instrument. The handpiece 2 has a longitudinal axis C. Here, one of directions parallel to the longitudinal axis C is a distal direction (direction of an arrow C1 in FIG. 1), and the direction opposite to the distal direction is a proximal direction (direction of an arrow C2 in FIG. 1). Here, the handpiece 2 is an ultrasonic coagulation-and-cutting treatment instrument configured to coagulate and cut, for example, a living tissue by using an ultrasonic vibration.

The handpiece 2 includes a holding unit 3. The holding unit 3 includes a cylindrical case portion 5 extending along the longitudinal axis C, a fixed handle 6 which is formed integrally with the cylindrical case portion 5, and a movable handle 7 which is turnably attached to the cylindrical case portion 5. The movable handle 7 turns around the position where the movable handle 7 is attached to the cylindrical case portion 5, so that the movable handle 7 performs an opening or closing motion relative to the fixed handle 6. The holding unit 3 also includes a rotational operation knob 8 attached to the distal direction side of the cylindrical case portion 5. The rotational operation knob 8 is rotatable around the longitudinal axis C relative to the cylindrical case portion 5. A supply operation input button 9 which is a supply operation input section is provided to the fixed handle 6.

The handpiece 2 includes a sheath 10 extending along the longitudinal axis C. When the sheath 10 is inserted into the rotational operation knob 8 and into the cylindrical case portion 5 from the distal direction side, the sheath 10 is attached to the holding unit 3. A jaw 11 is pivotably attached to the distal portion of the sheath 10. The movable handle 7 is connected to a movable cylindrical portion (not shown) of the sheath 10 inside the cylindrical case portion 5. The distal end of the movable cylindrical portion is connected to the jaw 11. If the movable handle 7 is opened or closed relative to the fixed handle 6, the movable cylindrical portion moves along the longitudinal axis C. As a result, the jaw 11 turns around the position where the jaw 11 is attached to the sheath 10. The sheath 10 and the jaw 11 are rotatable around the longitudinal axis C relative to the cylindrical case portion 5 together with the rotational operation knob 8.

The handpiece 2 also includes a vibrator case 12 extending along the longitudinal axis C. When the oscillator case 12 is inserted in the cylindrical case portion 5 from the proximal direction side, the vibrator case 12 is attached to the holding unit 3. Inside the cylindrical case portion 5, the vibrator case 12 is coupled to the sheath 10. The vibrator case 12 is rotatable around the longitudinal axis C relative to the cylindrical case portion 5 together with the rotational operation knob 8. One end of a cable 13 is connected to the oscillator case 12. The other end of the cable 13 is connected to a control unit 15. Here, the control unit 15 is an ultrasonic treatment control unit configured to control an ultrasonic treatment in the ultrasonic treatment system, and is an energy generator including, for example, a central processing unit (CPU) and an application specific integrated circuit (ASIC).

The handpiece 2 also includes a vibrating body unit 17. The vibrating body unit 17 extends along the longitudinal axis C from within the vibrator case 12 through an inside of the cylindrical case portion 5 and an inside of the sheath 10. The vibrating body unit 17 includes a treatment section 18 projecting toward the distal direction from the distal end of the sheath 10. The treatment section 18 is provided in the distal portion of the vibrating body unit 17. When the jaw 11 pivots relative to the sheath 10, the jaw 11 opens or closes relative to the treatment section 18. The vibrating body unit 17 is rotatable around the longitudinal axis C relative to the cylindrical case portion 5 together with the rotational operation knob 8.

Figure 3:
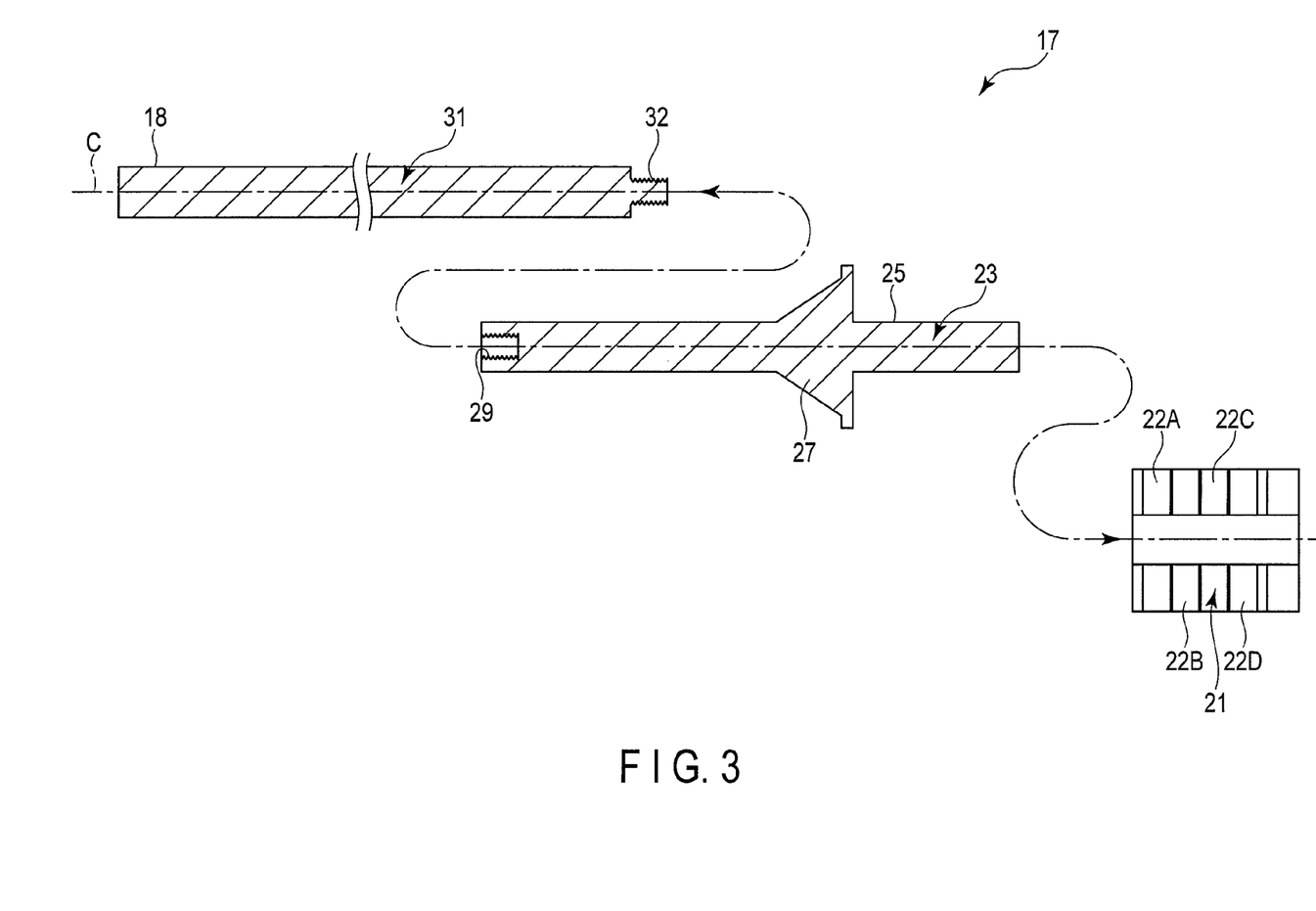
FIG. 3 is a sectional view showing a vibrating body unit according to the first embodiment disassembled into components.

FIG. 3 is a diagram showing the vibrating body unit 17 disassembled into components. As shown in FIG. 2 and FIG. 3, the vibrating body unit 17 includes an ultrasonic vibrator 21 which is an ultrasonic generator configured to generate an ultrasonic vibration when supplied with an electric current. The ultrasonic oscillator 21 includes (four, in the present embodiment) piezoelectric elements 22A to 22D which are configured to convert the electric current to a vibration. The vibrating body unit 17 also includes a columnar horn member 23 extending along the longitudinal axis C. The horn member 23 includes a vibrator attachment portion 25. Members such as the piezoelectric elements 22A to 22D that form the ultrasonic vibrator 21 are attached to the vibrator attachment portion 25. The ultrasonic vibrator 21 is provided to the proximal portion of the vibrating body unit 17, and is located inside the vibrator case 12.

The horn member 23 is provided with a sectional area changing portion 27 in which the sectional area perpendicular to the longitudinal axis C decreases toward the distal direction. An internal thread 29 is provided in the distal portion of the horn member 23. The vibrating body unit 17 includes a probe 31 extending along the longitudinal axis C to the distal direction side with respect to the horn member 23. An external thread 32 is provided in the proximal portion of the probe 31. When the external thread 32 is screwed into the internal thread 29, the probe 31 is connected to the distal direction side of the horn member 23. The horn member 23 extends up to the inside of the cylindrical case portion 5, and the probe 31 is connected to the horn member 23 inside the cylindrical case portion 5. The probe 31 extends through the inside of the sheath 10, and projects toward the distal direction from the distal end of the sheath 10. Thus, the treatment section 18 is located in the distal portion of the probe 31.

In the vibrating body unit 17, the ultrasonic vibration generated in the ultrasonic vibrator 21 is transmitted to the horn member 23. In the horn member 23 and the probe 31, the ultrasonic vibration is transmitted from the proximal direction toward the distal direction along the longitudinal axis C. That is, the horn member 23 and the probe 31 are ultrasonic transmitting portions which are configured to transmit the generated ultrasonic vibration along the longitudinal axis C. The treatment section 18 then conducts a treatment by the transmitted ultrasonic vibration. When the jaw 11 is closed relative to the treatment section 18, a grasping target such as a living tissue is grasped between the jaw 11 and the treatment section 18. When the vibrating body unit 17 vibrates while the grasping target is being grasped, frictional heat is generated between the treatment section 18 and the grasping target. The grasping target is coagulated and cut at the same time by the frictional heat. The vibrating body unit 17 vibrates at a frequency at which the proximal end (the proximal end of the ultrasonic vibrator 21) and the distal end (the distal end of the probe 31) become antinode positions. The ultrasonic vibration is a longitudinal vibration having a vibration direction and a transmission direction that are parallel to the longitudinal axis C.

As shown in FIG. 2, one end of each of two electric wiring lines 33A and 33B is connected to the ultrasonic vibrator 21. The control unit 15 includes a supply control section 35. The other end of each of the electric wiring lines 33A and 33B is connected to the supply controller 35. The supply state of the electric current to the ultrasonic vibrator 21 is controlled by the supply control section 35. One end of an electric signal line 39 is connected to the supply operation input button 9. The other end of the electric signal line 39 is connected to the supply control section 35. When the supply operation input button 9 is pressed, a supply operation to supply an electric current from the supply control section 35 is input. When the input of the supply operation is transmitted to the supply control section 35, the electric current is supplied to the ultrasonic vibrator 21 from the supply control section 35. That is, the control unit 15 which is the ultrasonic treatment control unit controls the vibrating state of the vibrating body unit 17 by controlling the supply of the electric current to the ultrasonic vibrator 21.

A storage section 36 such as an IC chip is provided in the vibrator case 12. Information regarding the handpiece 2 such as specification information regarding the handpiece 2 is stored in the storage 36. One end of an electric signal line 37 is connected to the memory section 36. The control unit 15 includes an information reading section 38. The other end of the electric signal line 37 is connected to the information reader 38.

The control unit 15 also includes an amplitude setting section 41, a calculation section 42, a current value setting section 43, a power switch 45, a judging section 46, a date-and-time update section 47, a number increasing section 48, and a number reset section 49. The power switch 45 is, for example, an operation button. The information reading section 38, the amplitude setting section 41, the calculator 42, the current value setting section 43, the judging section 46, the date-and-time update section 47, the number increasing section 48, and the number reset section 49 are formed by, for example, electronic circuits (e.g., a control circuit, a judging circuit, a reading circuit, and a calculating circuit) provided in the CPU and the ASIC. Details of processing in these parts will be described later.

Figure 4:
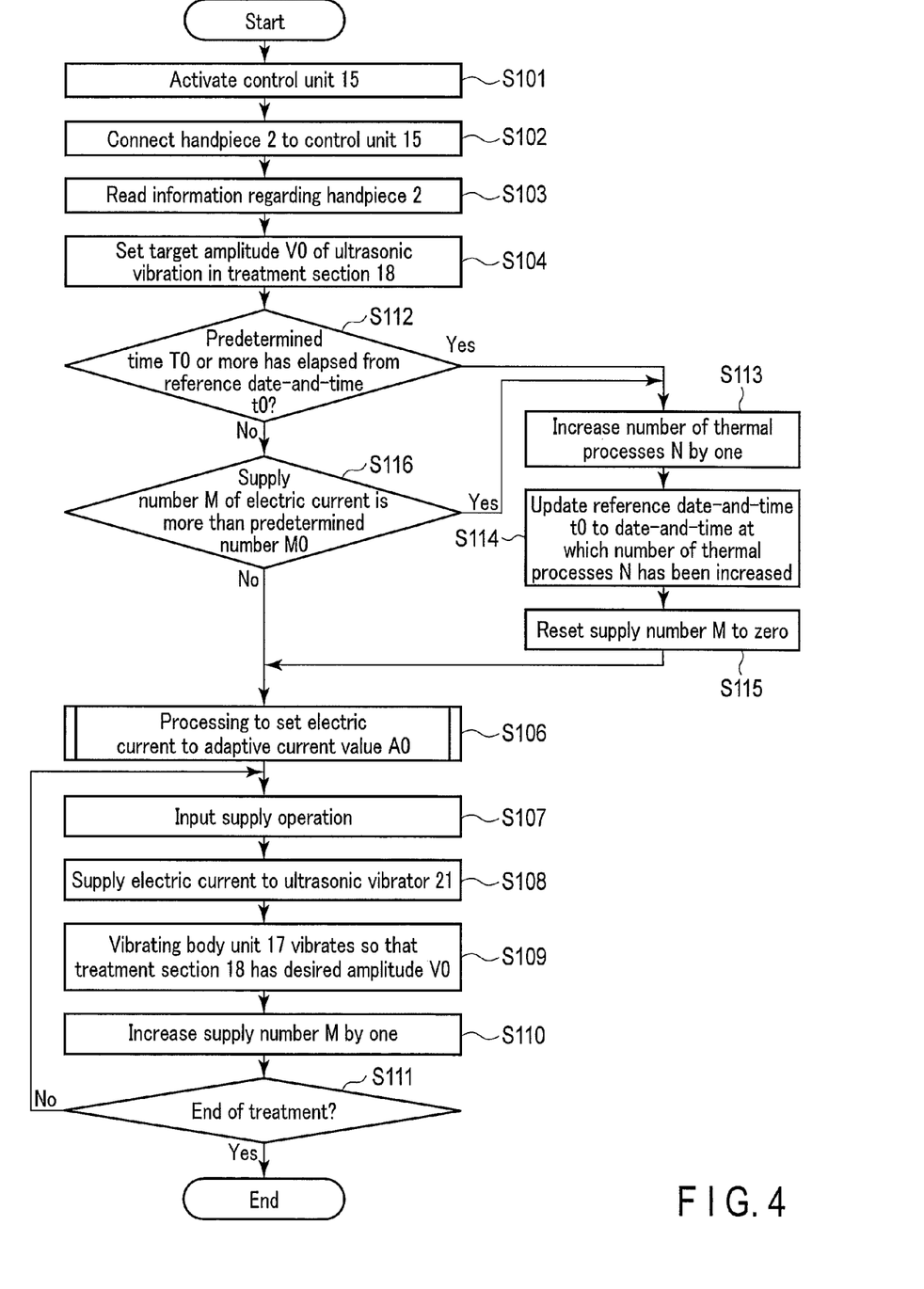
FIG. 4 is a flowchart illustrating a processing performed by a control unit and a handpiece when the treatment is conducted by a treatment section of the vibrating body unit according to the first embodiment.

Now, processing performed in the control unit 15 and the handpiece 2 when a treatment is conducted by the treatment section 18 of the vibrating body unit 17 is described with reference to a flowchart in FIG. 4. As shown in FIG. 4, when a treatment is conducted by the treatment section 18 of the vibrating body unit 17, the power switch 45 is first turned on, and the control unit 15 is activated (step S101). The handpiece 2 is then connected to the control unit 15 via the cable 13 (step S102). As a result, the ultrasonic vibrator 21 is electrically connected to the supply control section 35 via the electric wiring lines 33A and 33B. The storage section 36 is connected to the information reading section 38 via the electric signal line 37. The supply operation input button 9 is connected to the supply control section 35 via the electric signal line 39.

When the memory section 36 is connected to the information reading section 38, the information reading section 38 reads the information regarding the handpiece 2 stored in the storage section 36 (step S103). On the basis of the read information regarding the handpiece 2, the amplitude setting section 41 sets a target amplitude V0 of the ultrasonic vibration in the treatment section 18 of the vibrating body unit 17 (step S104). Here, the target amplitude V0 is the amplitude of the treatment section 18 at which the vibrating body unit 17 performs a vibration optimum for a treatment. When the treatment section 18 vibrates at the desired amplitude V0, a treatment target such as a living tissue is properly treated. The target amplitude V0 may be stored in the storage section 36. In this case, the amplitude setting section 41 sets the read target amplitude V0 as the target amplitude V0 of the ultrasonic vibration in the treatment section 18.

An elapse of time P since the production of the vibrating body unit 17 is recorded in the storage section 36. The handpiece 2 including the vibrating body unit 17 is sterilized by autoclave sterilization after use. Thus, one thermal treatment is conducted on the vibrating body unit 17 upon every sterilization. That is, after the completion of the treatment by the handpiece, one heat cycle is performed in the vibrating body unit 17. The number of thermal processes (number of heat cycles) N for the vibrating body unit 17 is stored in the memory section 36. The elapse of time P since production and the number of thermal processes N are information regarding the handpiece 2, and are read by the information reading section 38.

The calculation section 42 and the current value setting section 43 set an electric current to be supplied to the ultrasonic vibrator 21 to an adaptive current value A0 on the basis of the information regarding the handpiece 2 (information regarding the vibrating body unit 17) read by the information reading section 38 (step S106). The current value A of the electric current to be supplied to the ultrasonic vibrator 21 from the supply control section 35 is set on the basis of the elapse of time P since production and the number of thermal processes N.

Figure 5:
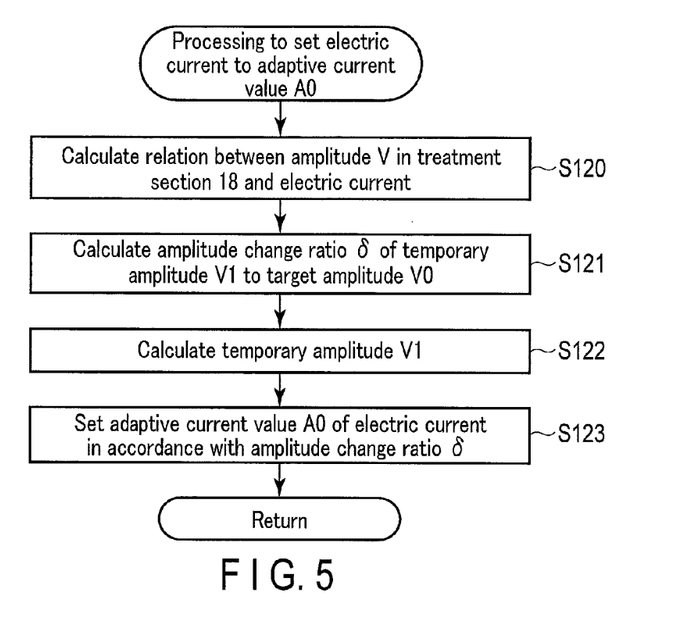
FIG. 5 is a flowchart illustrating a processing for setting an electric current to an adaptive current value in a calculation section and a current value setting section according to the first embodiment.

In a flowchart in FIG. 5, processing to set the electric current to be supplied to the ultrasonic vibrator 21 to the adaptive current value A0 is shown. As shown in FIG. 5, in the processing to set the current value A of the electric current, the calculation section 42 first calculates the relation between the amplitude of the treatment section 18 (the vibrating body unit 17) when the ultrasonic vibration is generated and the electric current to be supplied to the ultrasonic vibrator (ultrasonic generator) 21 on the basis of both the elapse of time P and the number of thermal processes N (step S120). That is, the elapse of time P and the number of thermal treatments N are used to calculate the influence of both the elapse of time P and the number of thermal processes N on the relation between the amplitude V of the ultrasonic vibration in the treatment section 18 and the electric current to be supplied to the ultrasonic vibrator 21. The current value setting section 43 sets the current value A of the electric current on the basis of the relation between the amplitude V of the treatment section 18 and the electric current calculated in the calculation section 42 in accordance with both the elapse of time P and the number of thermal processes N. In this instance, the current value setting section 43 sets the electric current to be supplied to the ultrasonic vibrator 21 to the adaptive current value A0 that brings the amplitude V of the ultrasonic vibration in the treatment section 18 to the target amplitude V0.

On the basis of the relation between the amplitude V of the treatment section 18 and the electric current to be supplied to the ultrasonic vibrator 21 calculated in step S120, a temporary amplitude V1 which is the amplitude V of the ultrasonic vibration in the treatment section 18 when the electric current having a reference current value A1 is supplied to the ultrasonic vibrator 21 is calculated (step S122). In this instance, the temporary amplitude V1 is calculated in accordance with both the elapse of time P since production and the number of thermal treatments N. The calculation section 42 also calculates an amplitude change ratio δ of the temporary amplitude V1 to the target amplitude V0 (step S121). The temporary amplitude V1 is calculated by the use of the desired amplitude V0 and the amplitude change ratio δ. The reference current value A1 is stored in the storage section 36, and is read by the information reading section 38 as the information regarding the handpiece 2. Here, a condition in which the elapse of time P is zero and the number of thermal processes N is zero is an initial condition. In the present embodiment, a calculation is performed using, as the reference current value A1, the current value A of the electric current that brings the amplitude V of the ultrasonic vibration in the treatment section 18 to the target amplitude V0 in the initial condition.

In the vibrating body unit 17, the piezoelectric elements 22A to 22D that form the ultrasonic vibrator 21 deteriorate, for example, due to the elapse of time since production. As a result of the deterioration of the piezoelectric elements 22A to 22D, the vibrating characteristics of the vibrating body unit 17 change, and the amplitude V of the ultrasonic vibration in the treatment section 18 changes compared to that at the time of production. Here, the relation

[Expression 1]

$$\alpha = Q1 \ln(P) + Q2 \quad (1)$$

is satisfied, wherein $\alpha$ is an amount of change in the amplitude V resulting from the elapse of time P since production. Here, Q1 and Q2 are constants determined by, for example, the characteristics of the piezoelectric elements 22A to 22D, and are recorded in the storage section 36. According to Expression (1), the amplitude V of the ultrasonic vibration in the treatment section 18 of the vibrating body unit 17 increases as time elapses since production.

In the vibrating body unit 17, the piezoelectric elements 22A to 22D that form the ultrasonic vibrator 21 deteriorate, for example, due to the thermal process by the autoclave sterilization. As a result of the deterioration of the piezoelectric elements 22A to 22D, the vibrating characteristics of the vibrating body unit 17 change, and the amplitude V of the ultrasonic vibration in the treatment section 18 changes compared to that at the time of production. Here, the relation

[Expression 2]

$$\beta = R1 \ln(N) + R2 \quad (2)$$

is satisfied, wherein $\beta$ is an amount of change in the amplitude V resulting from the number of thermal processes N. Here, R1 and R2 are constants determined by, for example, the characteristics of the piezoelectric elements 22A to 22D, and are stored in the storage section 36. According to Expression (2), the amplitude V of the ultrasonic vibration in the treatment section 18 increases upon every thermal process.

The amplitude change ratio $\delta$ of the temporary amplitude V1 to the target amplitude V0 can be found by the use of Expression (1) and Expression (2). When the amplitude change ratio $\delta$ is found, the amount of change a in the amplitude V resulting from the elapse of time P is converted to a parameter N' corresponding to the number of thermal processes N. The use of the number of thermal processes N and the parameter N' leads to

[Expression 3]

$$\delta = R1 \ln(N' + N) + R2 \quad (3)$$

The relation between the amount of change a and the parameter N' is

[Expression 4]

$$\alpha = R1 \ln(N') + R2 \quad (4).$$

This leads to

[Expression 5]

$$N' = \exp\left(\frac{\alpha - R2}{R1}\right). \quad (5)$$

When Expression (1) and Expression (5) are substituted for Expression (3),

[Expression 6]

$$\delta = R1 \ln\left(\exp\left(\frac{Q1 \ln(P) + Q2 - R2}{R1}\right) + N\right) + R2, \quad (6)$$

and the amplitude change ratio $\delta$ of the temporary amplitude V1 to the target amplitude V0 is found. The temporary amplitude V1 is

[Expression 7]

$$V1 = V0(1 + \delta) \quad (7)$$

As described above, Expression (6) and Expression (7) which are relational expressions using the elapse of time P and the number of thermal processes N as parameters are used to calculate the temporary amplitude V1 and the amplitude change ratio $\delta$ of the temporary amplitude V1 to the target amplitude V0. According to Expression (6) and Expression (7), the amplitude change ratio $\delta$ increases as the elapse of time P increases. The amplitude change ratio $\delta$ also increases as the number of thermal processes N increases. Therefore, the temporary amplitude V1 becomes greater than the target amplitude V0.

As shown in FIG. 5, the current value setting section 43 sets the current value A of the electric current to be supplied to the ultrasonic vibrator 21 to the adaptive current value A0 on the basis of the amplitude change ratio $\delta$ (step S123). Here, when the electric current having the reference current value A1 is supplied after time has elapsed since production and several thermal processes have been conducted, the treatment section 18 vibrates at the temporary amplitude V1 greater than the desired amplitude V0. Thus, after time has elapsed since production and several thermal treatments have been conducted, the adaptive current value A0 that brings the amplitude V of the treatment section 18 to the target amplitude V0 is lower than the reference current value A1.

Here, the amplitude of the vibrating body unit 17 including the treatment section 18 is proportionate to the current output from the supply control section 35 (i.e. the electric current to be supplied to the ultrasonic vibrator 21). Due to the deterioration of the piezoelectric elements 22A to 22D resulting from the thermal processes, the temporary amplitude V1 which is the amplitude of the treatment section 18 when the electric current having the reference current value A1 is supplied to the ultrasonic vibrator 21 is $(1+\delta)V0$, as described in accordance with Expression (7). Therefore, if the adaptive current value A0 is

[Expression 8]

$$A0 = \frac{1}{1 + \delta} \times A1, \quad (8)$$

the amplitude of the treatment section 18 can be kept at the target amplitude V0.

If the adaptive current value A0 is set, a supply operation is input by the pressing of the supply operation input button 9 as shown in FIG. 4 (step S107). An electric current having the adaptive current value A0 is supplied to the ultrasonic vibrator 21 from the supply control section 35 (step S108). The supply control section 35 controls the supply of the electric current so that the constant electric current having the adaptive current value A0 is supplied to the ultrasonic vibrator 21. That is, the supply control section 35 performs constant electric current control at the adaptive current value A0.

As a result of the supply of the electric current having the adaptive current value A0 to the ultrasonic vibrator 21, ultrasonic vibration is generated in the ultrasonic vibrator 21, and the vibrating body unit 17 vibrates so that the treatment section 18 may have the target amplitude V0 (step S109). The treatment section 18 uses the ultrasonic vibration to treat a grasping target such as a living tissue. A supply number M of the electric current to the ultrasonic vibrator 21 from the supply control section 35 is stored in the storage section 36. When an electric current is supplied from the supply control section 35 in response to the input of the supply operation, the supply control Section 35 increases the supply number M by one (step S110). When the supply number M is increased, the increased supply number M is recorded in the memory section 36.

When the treatment is continued (step S111—No), the processing returns to step S107, and steps S107 to S110 are repeated. Thus, the supply number M is increased by one whenever an electric current is supplied froth the supply control section 35.

A reference date-and-time t0 to be a reference is stored in the storage section 36. As shown in FIG. 4, the judging section 46 judges whether a predetermined time TO or more (e.g., 12 hours or more) has elapsed from the reference date-and-time t0 to a current date-and-time t1 (step S112). The judgment in step S112 is made before the processing to set the current value A of the electric current to be supplied to the ultrasonic vibrator 21 (i.e., step S106).

The reference date-and-time t0 is updated by the date-and-time update section 47. When an electric current is supplied from the supply control section 35, the reference date-and-time t0 is updated to the date-and-time at which the electric current is supplied. In general, during a treatment using ultrasonic waves, supply operations are frequently input, and electric currents are frequently supplied to the ultrasonic vibrator 21 from the supply control section 35. Thus, during a treatment, there is a short time between a date-and-time at which an electric current is supplied from the supply control section 35 and a date-and-time at which an electric current is next supplied from the supply control section 35. On the other hand, after the treatment has finished, the time from the end of the treatment to the start of the next treatment is long. Therefore, there is a long time between the date-and-time at which an electric current is last supplied from the supply control section 35 in a certain treatment and the date-and-time at which an electric current is first supplied from the supply control section 35 in the next treatment. The thermal process by the autoclave sterilization is conducted between a certain treatment and the next treatment. Thus, the reference date-and-time t0 is updated at the date-and-time at which the supply control section 35 supplies the electric current, so that whether the thermal process by the autoclave sterilization has been conducted between the reference date-and-time t0 and the current date-and-time t1 is effectively judged by the time elapsed since the reference date-and-time t0.

When the predetermined time TO or more has elapsed since the reference date-and-time t0 (step S112-Yes), it is judged that the thermal process has been conducted since the reference date-and-time t0. Thus, the number increasing section 48 increases the number of thermal processes N by one (step S113). The increased number of thermal processes N is stored in the storage section 36.

When the number of thermal processes N has been increased, the time update section 47 updates the reference date-and-time t0 to the date-and-time at which the number of thermal processes has been increased (step S114). During the treatment, unexpected situations may occur before the supply of the electric current from the supply control section 35; for example, the power supply of the control unit 15 may be cut, or the cable 13 may be disconnected from the control unit. In the case where the update of the reference date-and-time t0 in step S114 is not performed, the number of thermal treatments N is again increased when the control unit 15 is activated after the occurrence of the unexpected situations. That is, the number of thermal processes N may be increased when a thermal process is not actually conducted. Thus, in the present embodiment, the reference date-and-time t0 is updated in step S114, so that the number of thermal processes N is not again increased until the start of the next treatment after the increase of the number of thermal processes N. That is, the number of thermal processes N is not again increased in the treatment being conducted at present (during the current treatment). Therefore, the calculation section 42 performs a calculation using the number of thermal processes N that is highly correct.

When the number of thermal processes N is increased, the number reset section 49 resets the supply number M of the electric current from the supply control section 35 to zero (step S115). After steps S113 to S115 are performed, processing to set the current value A of the electric current is performed in step S106. In this instance, the calculation section 42 and the current value setting section 43 use the increased number of thermal processes N to calculate the relation between the amplitude V of the ultrasonic vibration and the electric current based on both the elapse of time P and the number of thermal processes N, and also set the electric current to be supplied to the ultrasonic vibrator 21 to the adaptive current value A0.

When the predetermined time TO or more has not elapsed since the reference date-and-time t0 (step S112—No), the judging section 46 judges whether the supply number M of the electric current from the supply control section 35 is more than a predetermined number MO (step S116). The judgment in step S116 is made before the processing to set the current value A of the electric current to be supplied to the ultrasonic vibrator 21 (i.e., step S106).

When a long time is required for one treatment, there may not be a long time before the next treatment. In this case, the predetermined time TO or more has not elapsed from the reference date-and-time t0 to the current date-and-time t1. However, after the completion of the treatment, the thermal process by the autoclave sterilization is conducted before the start of the next treatment. Therefore, the thermal process that has been actually conducted may not be added to the number of thermal processes N. Thus, in the present embodiment, the judgment based on the supply number M of the electric current is made in step S116. In one treatment using ultrasonic vibration, electric currents are supplied from the supply control section 35 at least the supply number M more than the predetermined number MO. Thus, the predetermined number MO is compared with the supply number M, so that even when the previous treatment has required a long time, whether the thermal treatment by the autoclave sterilization has been conducted is effectively judged by the supply number M of the electric current. In step S110, the supply number M is successively increased each time an electric current is supplied.

When the supply number M of the electric current is more than the predetermined number M0 (step S116-Yes), it is judged that the thermal process has been conducted since the reference date-and-time t0. Thus, the above-described steps S113 to S115 are performed. After steps S113 to S115 have been performed, the processing to set the current value A of the electric current is performed in step S106. In this instance, the calculation section 42 and the current value setting section 43 use the increased number of thermal processes N to calculate the relation between the amplitude V of the ultrasonic vibration and the electric current based on both the elapse of time P and the number of thermal processes N, and also set the electric current to be supplied to the ultrasonic vibrator 21 to the adaptive current value A0.

In the present embodiment, the supply number M of the electric current is reset to zero in step S115, so that the number of thermal processes N is not again increased until the start of the next treatment after the increase of the number of thermal processes N. That is, the number of thermal processes N is not again increased in the treatment being conducted at present (during the current treatment). Therefore, the calculation section 42 performs a calculation using the number of thermal processes N that is highly correct.

When the supply number M of the electric current is not more than the predetermined number M0 (step S116—No), it is judged that the thermal process has not been conducted since the reference date-and-time t0. Thus, the above-described steps S113 to S115 are not performed, and the processing to set the current value A of the electric current is performed in step S106. In this instance, the calculation section 42 and the current value setting section 43 use the number of thermal processes N that is not increased to calculate the relation between the amplitude V of the ultrasonic vibration and the electric current based on both the elapse of time P and the number of thermal processes N, and also set the electric current to be supplied to the ultrasonic vibrator 21 to the adaptive current value A0.

As described above, in the ultrasonic treatment system 1 and the ultrasonic treatment control unit 15 according to the present embodiment, the relation between the amplitude V of the ultrasonic vibration in the treatment section 18 and the electric current to be supplied to the ultrasonic vibrator 21 based on both the elapse of time P and the number of thermal processes N is calculated. On the basis of the relation between the amplitude V of the ultrasonic vibration and the electric current that changes in accordance with the elapse of time P and the number of thermal processes N, the current value A of the electric current is set to the adaptive current value A0 that brings the amplitude V of the ultrasonic vibration in the treatment section 18 to the target amplitude V0. Since the electric current having the adaptive current value A0 is supplied to the ultrasonic vibrator 21, the vibrating body unit 17 constantly vibrates so that the treatment section 18 has the target amplitude V0, and the vibrating characteristics of the vibrating body unit 17 do not change due to the elapse of time P since production and the number of thermal treatments N. Thus, the amplitude V of the treatment section 18 is always kept at the constant desired amplitude V0 regardless of the elapse of time P since production and the number of thermal processes N. Therefore, the treatment performance in the treatment section 18 can be maintained regardless of the elapse of time P since production and the number of thermal processes N.

Modifications

Figure 6:
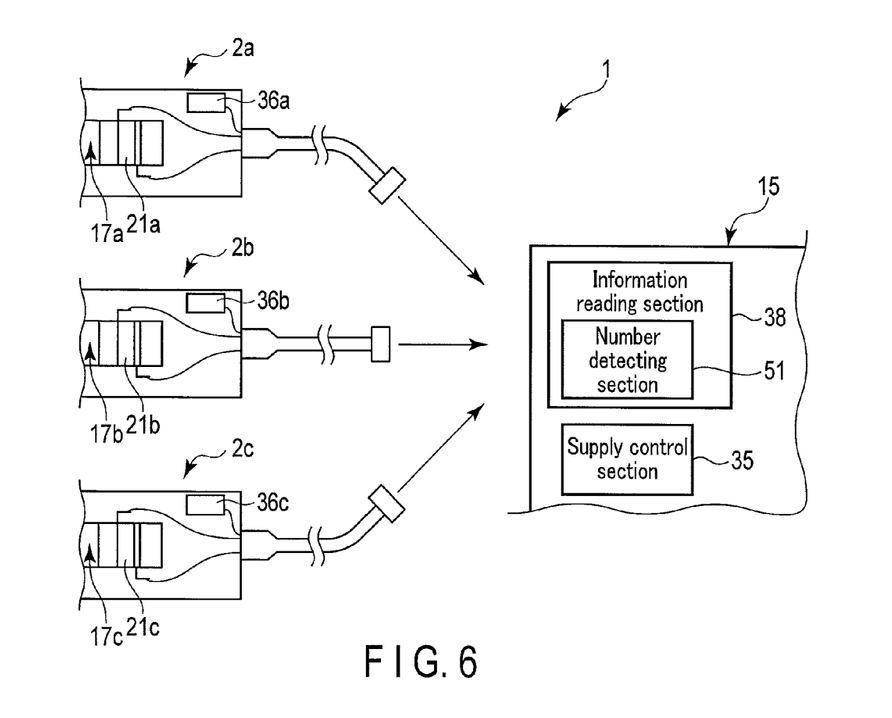
FIG. 6 is a schematic diagram showing an ultrasonic treatment system according to a first modification.

As in a first modification shown in FIG. 6, handpieces 2a to 2c which are ultrasonic treatment instruments (three ultrasonic treatment instruments in the present modification) are connectable to the control unit 15 which is the ultrasonic treatment control unit. When an ultrasonic treatment is conducted, one of the handpieces 2a to 2c is connected to the control unit 15. In the handpiece (one of 2a to 2c) connected to the control unit 15, an ultrasonic vibrator (one of 21a to 21c) is electrically connected to the supply control section 35, and a storage section (one of 36a to 36c) is electrically connected to the information reading section 38.

In each of the handpieces 2a to 2c according to the present modification, the serial number of a vibrating body unit (one of 17a to 17c) is stored in the storage section (one of 36a to 36c). The information reader 38 is provided with a number detecting section 51 configured to detect the serial number of the vibrating body unit (one of 17a to 17c) in which the ultrasonic vibrator (one of 21a to 21c) is connected to the supply controller 35. For example, when the handpiece 2a is connected to the control unit 15, the number detector 51 detects the serial number of the vibrating body unit 17a from the storage 36a.

In general, in the production of the vibrating body units 17a to 17c, uniform vibrating characteristics in all the vibrating body units 17a to 17c are difficult to obtain due to, for example, characteristic variation of the piezoelectric elements 22A to 22D according to the vibrating body units 17a to 17c. Thus, the vibrating characteristics of the vibrating body units 17a to 17c vary according to the serial number. For example, target current values Aa0 to Ac0 which are current values A to bring the treatment sections 18a to 18c of the vibrating body units 17a to 17c in the initial condition (the condition in which the elapse of time P is zero and the number of thermal processes N is zero) vary according to the serial numbers of the vibrating body units 17a to 17c.

The calculator 42 calculates the influence of both the elapse of time P and the number of thermal processes N on the relation between the amplitude V of the ultrasonic vibration in the corresponding treatment section (one of 18a to 18c) and the electric current in accordance with the detected serial number. That is, a parameter regarding the vibrating characteristics corresponding to the vibrating body unit (one of 17a to 17c) of the detected serial number is used to calculate the relation between the amplitude V of the ultrasonic vibration in the corresponding treatment section (one of 18a to 18c) and the electric current based on both the elapse of time P and the number of thermal processes N. For example, when the handpiece 2a is connected to the control unit 15, an amplitude change ratio δa is

[Expression 9]

$$\delta a = Ra1\ln\left(\exp\left(\frac{Qa1\ln(P) + Qa2 - Ra2}{Ra1}\right) + N\right) + Ra2. \qquad (9)$$

On the basis of the amplitude change ratio δa, the current value setting section 43 sets the current value A of the electric current to the adaptive current value Aa0 that brings the amplitude V of the treatment section 18a to the target amplitude V0. On the other hand, when the handpiece 2b is connected to the control unit 15, an amplitude change ratio δb is

[Expression 10]

$$\delta b = Rb1 \ln\left(\exp\left(\frac{Qb1\ln(P) + Qb2 - Rb2}{Rb1}\right) + N\right) + Rb2. \quad (10)$$

On the basis of the amplitude change ratio δb, the current value setting section 43 sets the current value A of the electric current to the adaptive current value Aa0 that brings the amplitude V of the treatment section 18b to the desired amplitude V0. Here, Qa1, Qa2, Ra1, Ra2, Qb1, Qb2, Rb1, and Rb2 are constants determined by the serial numbers.

As described above, in the present modification, owing to the control unit 15, it is possible to supply electric current having the corresponding adaptive current value (one of Aa0 to Ac0) in accordance with the elapse of time P and the number of thermal processes N for each of the vibrating body units 17a to 17c having the serial numbers. Therefore, owing to the control unit 15, the constant desired amplitude V0 is always maintained in each of the treatment sections 18a to 18c of the vibrating body units 17a to 17c having the serial numbers.

Although the handpiece 2 which coagulates and cuts the grasping target between the jaw 11 and the treatment section 18 by the ultrasonic vibration is connected to the control unit 15 in the first embodiment, this is not a limitation. For example, as in a second modification shown in FIG. 7, an ultrasonic suction treatment instrument 55 may be connected to the control unit 15. As in the handpiece, the vibrator case 12, the holding unit 3, and the vibrating body unit 17 are provided in the ultrasonic suction treatment instrument 55. However, the holding unit 3 is only provided with the cylindrical case portion 5, and is not provided with the fixed handle 6, the movable handle 7, and the rotational operation knob 8. The vibrating body unit 17 includes the ultrasonic probe 31, the horn member 23, and the ultrasonic vibrator 21, but instrument is not provided with the jaw 11.

Figure 7:
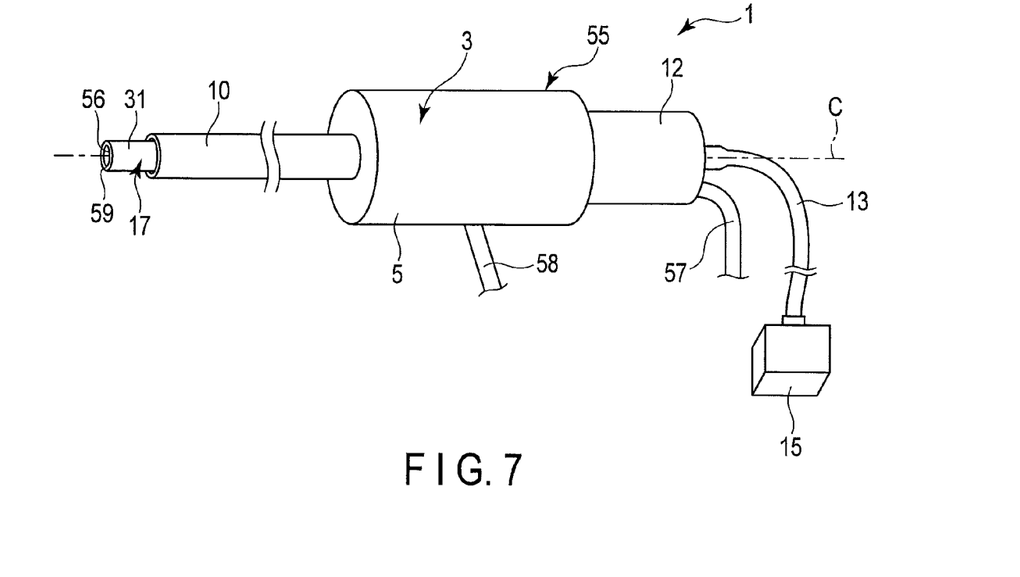
FIG. 7 is a perspective view schematically showing an ultrasonic treatment system according to a second modification.

In the present modification, a suction path 56 extends through an inside of the vibrating body unit 17 along the longitudinal axis C. One end of a suction tube 57 is connected to the suction path 56. One end of a liquid supply tube 58 is connected to a cavity between the sheath 10 and the probe 31. When a treatment by an ultrasonic vibration is conducted, the vibrating body unit 17 is vibrated by the ultrasonic vibration and water passing through an inside of the liquid supply tube 58 and through the cavity between the probe 31 and the sheath 10 is supplied from the distal end of the sheath 10. As a result, cavitation is caused in the vicinity of a treatment section 59 provided on a distal surface of the probe 31, and a treatment target such as a living tissue is shattered. The shattered treatment target is then suctioned through the suction path 56 and an inside of the suction tube 57. In this instance, as in the first embodiment, the amplitude V in the treatment section 59 is set to the desired amplitude V0.

Figure 8:
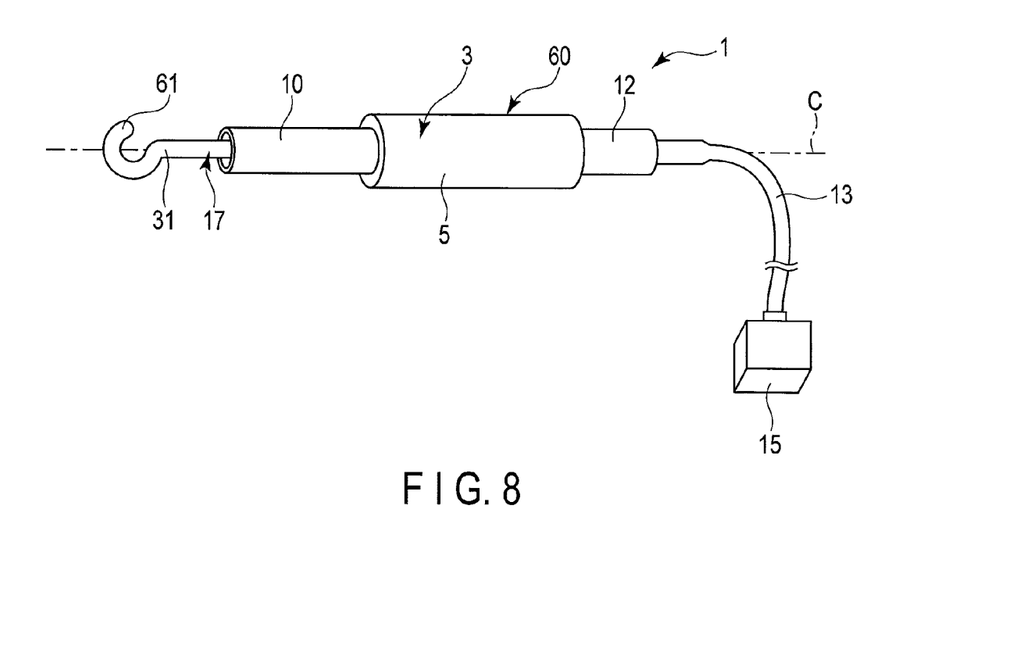
FIG. 8 is a perspective view schematically showing an ultrasonic treatment system according to a third modification.

As in a third modification shown in FIG. 8, an ultrasonic resection treatment instrument 60 may be connected to the control unit 15. In the present modification, the jaw 11, the fixed handle 6, the movable handle 7, and the rotational operation knob 8 are not provided, as in the second modification. In the present modification, a hook-shaped portion 61 which is a treatment section is provided in the distal portion of the probe 31. When a treatment by an ultrasonic vibration is conducted, the vibrating body unit 17 is vibrated by the ultrasonic vibration while a treatment target such as a living tissue is hooked to the hook-shaped portion 61. As a result, the hooked treatment target is resected. At the same time, as in the first embodiment, the amplitude V in the hook-shaped portion (treatment section) 61 is set to the desired amplitude V0. According to the second modification and the third modification, the treatment instrument connected to the control unit 15 has only to be an ultrasonic treatment instrument (2; 55; 60) which conducts a treatment using an ultrasonic vibration.

Although the control unit 15 sets, to the target amplitude V0, the amplitude of the treatment section 18 at which the vibrating body unit 17 performs optimum vibration suitable to a treatment in the first embodiment, this is not a limitation. For example, in the calculation and electric current control in the control unit 15, the amplitude of the vibrator attachment portion 25 at which the vibrating body unit 17 performs optimum vibration suitable to a treatment may be the target amplitude (V0). In this case as well, as in the first embodiment, the electric current to be supplied to the ultrasonic vibrator 21 is controlled so that the vibrator attachment portion 25 of the vibrating body unit 17 will have the desired amplitude (V0). When the vibrator attachment portion 25 vibrates at the target amplitude (V0), the treatment performance in the treatment section 18 is ensured. Therefore, the amplitude setting section 41 has only to set, as the target amplitude (V0), the amplitude of a part of the vibrating body unit 17 when the vibrating body unit 17 performs optimum vibration by the ultrasonic vibration.

Although the storage section 36 is provided inside the vibrator case 12 in the first embodiment, this is not a limitation. The storage section 36 may be provided inside the holding unit 3 or may be provided inside the cable 13. Alternatively, the storage section 36 may be provided inside the control unit 15. In this case, the information reading section 38 reads, from the storage section 36 of the control unit 15, information such as the elapse of time P since the production of the vibrating body unit 17 and the number of thermal processes N of the vibrating body unit 17.

Although the number of thermal processes N is automatically increased in the first embodiment, this is not a limitation. For example, the number of thermal processes N may be increased by the surgeon's operation.

As above, an ultrasonic treatment system (1) includes a vibrating body unit (17; 17a to 17c) including an ultrasonic generator (21) configured to generate an ultrasonic vibration when supplied with an electric current and an ultrasonic transmitting portion (23, 31) configured to transmit the generated ultrasonic vibration, an amplitude setting section (41) configured to set, as a target amplitude (V0), an amplitude at which the vibrating body unit (17; 17a to 17c) performs an optimum vibration by the ultrasonic vibration, a storage section (36; 36a to 36c) configured to store an elapse of time (P) since the production of the vibrating body unit (17; 17a to 17c) and the number of thermal sterilization processes (N) conducted on the vibrating body unit (17; 17a to 17c), a calculation section (42) configured to calculate the relation between the amplitude (V) of the vibrating body unit (17; 17a to 17c) when the ultrasonic vibration is generated and the electric current to be supplied to the ultrasonic generator (21) on the basis of both the elapse of time (P) and the number of thermal processes (N), a current value setting section (43) configured to set a current value (A) of an electric current to an adaptive current value (A0; Aa0 to Ac0) that brings the amplitude (V) of the vibrating body unit (17; 17a to 17c) to the desired amplitude (V0) on the basis of the relation between the amplitude (V) of the vibrating body unit (17; 17a to 17c) and the electric current calculated by the calculation section (42), and a supply control section (35) configured to control the supply of the electric current to the ultrasonic generator (21) so that the electric current having the adaptive current value (A0; Aa0 to Ac0) is supplied.

Characteristic matters are additionally described below.

Notes (Additional Note 1)

An ultrasonic treatment control unit configured to control a vibrating state of a vibrating body unit by an ultrasonic vibration, the vibrating body unit including an ultrasonic generator configured to generate the ultrasonic vibration when supplied with an electric current, and an ultrasonic transmitting portion configured to transmit the generated ultrasonic vibration, the ultrasonic treatment control unit comprising:

an information reading section configured to read an elapse of time since a production of the vibrating body unit and a number of thermal processes conducted every sterilization of the vibrating body unit;

an amplitude setting section configured to set, as a target amplitude, an amplitude at which the vibrating body unit performs an optimum vibration by the ultrasonic vibration;

a calculation section configured to calculate the relation between the amplitude of the vibrating body unit when the ultrasonic vibration is generated and the electric current to be supplied to the ultrasonic generator on the basis of both the elapse of time and the number of thermal processes;

a current value setting section configured to set the electric current to be supplied to the ultrasonic generator to an adaptive current value that brings the amplitude of the vibrating body unit to the target amplitude on the basis of the relation between the amplitude of the vibrating body unit and the electric current calculated by the calculation section; and a supply control section configured to control a supply of the electric current to the ultrasonic generator so that the electric current having the adaptive current value is supplied.

(Additional Note 2)

An ultrasonic treatment system comprising:

the ultrasonic treatment control unit according to claim 1; and the vibrating body unit including the ultrasonic generator and the ultrasonic transmitting portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment system comprising:
a vibrating body including:
an ultrasonic generator configured to generate an ultrasonic vibration when supplied with an electric current; and
an ultrasonic transmitting portion configured to transmit the generated ultrasonic vibration;
a memory configured to store: (i) an elapse of time since a production of the vibrating body, and (ii) a number of thermal processes by sterilization of the vibrating body; and a processor operatively coupled to the memory, the processor programmed to:
calculate a relation between: (i) an amplitude of the vibrating body when the ultrasonic vibration is generated, and (ii) the electric current to be supplied to the ultrasonic generator, based on both the elapse of time and the number of thermal processes;
set the electric current to be supplied to the ultrasonic generator to an adaptive current value that controls the amplitude of the vibrating body to be a target amplitude, based on the calculated relation between the amplitude of the vibrating body and the electric current; and
control a supply of the electric current to the ultrasonic generator in order to supply the electric current having the adaptive current value.

2. The ultrasonic treatment system according to claim 1, wherein the processor is programmed to:
calculate: (i) a temporary amplitude based on both the elapse of time and the number of thermal processes, the temporary amplitude being the amplitude of the vibrating body when the electric current having a reference current value is supplied, and (ii) an amplitude change ratio of the temporary amplitude to the target amplitude; and
set the adaptive current value of the electric current based on the amplitude change ratio.

3. The ultrasonic treatment system according to claim 2, wherein when an initial condition is the elapse of time is zero and the number of thermal processes is zero, the processor is programmed to calculate the temporary amplitude and the amplitude change ratio based on the reference current value being a current value of the electric current that controls the amplitude of the vibrating body in the initial condition to be the target amplitude.

4. The ultrasonic treatment system according to claim 3, wherein the processor is programmed to:
calculate the temporary amplitude and the amplitude change ratio based on a relational expression in which the elapse of time and the number of thermal processes are parameters such that the temporary amplitude is greater than the target amplitude; and
set the adaptive current value lower than the reference current value based on the amplitude change ratio.

5. The ultrasonic treatment system according to claim 1, wherein:
the vibrating body includes a plurality of vibrating bodies, each vibrating body of the plurality of vibrating bodies having a different serial number;
the processor is electrically connected to the ultrasonic generator of one of the plurality of vibrating bodies; and
the processor is programmed to:
detect the serial number of the one of the plurality of vibrating bodies in which the ultrasonic generator is connected to the processor; and
calculate a relation of the one of the plurality of vibrating bodies having the detected serial number, the relation being between the amplitude of the ultrasonic vibration in the one of the plurality of vibrating bodies and the electric current, based on both the elapse of time and the number of thermal processes.

6. The ultrasonic treatment system according to claim 1, wherein:
the memory stores a reference date-and-time; and
the processor is programmed to:
increase the number of thermal processes by one when a predetermined time or more has elapsed from the reference date-and-time in a setting to the adaptive current value; and
update the reference date-and-time at a date-and-time at which: (i) the electric current is supplied, and (ii) the number of thermal processes is increased.

7. The ultrasonic treatment system according to claim 6, wherein:
the memory stores a supply number of the electric current to the ultrasonic generator; and
the processor is programmed to:
increase the number of thermal processes by one when: (i) the predetermined time or more has not elapsed from the reference date-and-time, and (ii) the supply number of the electric current is more than a predetermined number in the setting to the adaptive current value; and
reset the supply number of the electric current to zero when the number of thermal processes is increased.

8. The ultrasonic treatment system according to claim 7, wherein when the number of thermal processes is increased in the setting to the adaptive current value, the processor is programmed to use the increased number of thermal processes to calculate the relation between the amplitude of the ultrasonic vibration in the vibrating body and the electric current, based on both the elapse of time and the number of thermal processes.

9. The ultrasonic treatment system according to claim 1, wherein:
the vibrating body extends along a longitudinal axis;
the ultrasonic generator is provided in a proximal portion of the vibrating body;
the vibrating body includes a treatment portion in a distal portion; and
the ultrasonic transmitting portion is configured to transmit the ultrasonic vibration from a proximal direction to a distal direction along the longitudinal axis.

* * * * *